(12) United States Patent
Usuda et al.

(10) Patent No.: US 10,690,905 B2
(45) Date of Patent: Jun. 23, 2020

(54) IMAGING MODULE, ENDOSCOPE, AND METHOD OF MANUFACTURING IMAGING MODULE

(71) Applicant: Fujikura Ltd., Tokyo (JP)

(72) Inventors: Hideaki Usuda, Sakura (JP); Kenichi Nakatate, Sakura (JP)

(73) Assignee: FUJIKURA LTD., Tokyo (JP)

( * ) Notice: Subject to any disclaimer, the term of this patent is extended or adjusted under 35 U.S.C. 154(b) by 221 days.

(21) Appl. No.: 15/434,302

(22) Filed: Feb. 16, 2017

(65) Prior Publication Data

US 2017/0269349 A1    Sep. 21, 2017

(30) Foreign Application Priority Data

Mar. 16, 2016    (JP) .................................. 2016-052157

(51) Int. Cl.
*G02B 23/24*    (2006.01)
*A61B 1/05*    (2006.01)
*H04N 5/225*    (2006.01)
*G02B 7/02*    (2006.01)

(52) U.S. Cl.
CPC .......... *G02B 23/2484* (2013.01); *A61B 1/051* (2013.01); *H04N 5/2254* (2013.01); *G02B 7/02* (2013.01); *H04N 2005/2255* (2013.01)

(58) Field of Classification Search
CPC .......... H04N 5/2254; H04N 2005/2255; A61B 1/05; A61B 1/051; A61B 1/0011; A61B 1/00105; G02B 23/2484; G02B 7/02
See application file for complete search history.

(56) References Cited

U.S. PATENT DOCUMENTS

| 3,951,522 A * | 4/1976 | Hashimoto ............... G02B 7/10 359/694 |
| 4,154,510 A * | 5/1979 | Katagiri ................... G02B 7/04 359/704 |
| 5,218,479 A * | 6/1993 | Chiou ....................... G02B 7/10 359/700 |
| 2005/0182299 A1* | 8/2005 | D'Amelio .......... A61B 1/00096 600/175 |

(Continued)

FOREIGN PATENT DOCUMENTS

| EP | 2680059 A1 | 1/2014 |
| JP | 5-293080 A | 11/1993 |

(Continued)

*Primary Examiner* — John P Leubecker
*Assistant Examiner* — Shankar Raj Ghimire
(74) *Attorney, Agent, or Firm* — Westerman, Hattori, Daniels & Adrian, LLP (57) ABSTRACT

An imaging module of the invention includes: an image-sensing unit that includes an image-sensing device; a lens that has a front end and is optically connected to the image-sensing device; and a frame that is fixed in position with respect to the image-sensing device and includes a lens barrel having an insertion space, into which the front end is to be inserted in at least an optical axis direction. In a state where movement of the lens in a direction intersecting with the optical axis direction is limited, the insertion space is capable of receiving the lens in the direction such that the lens approaches the image-sensing device. The lens is fixed to the lens barrel at a position at which the lens is optically connected to the image-sensing device.

6 Claims, 9 Drawing Sheets

(56) References Cited

U.S. PATENT DOCUMENTS

| | | | |
|---|---|---|---|
| 2005/0265716 A1* | 12/2005 | Tsuji | G02B 7/102 396/542 |
| 2007/0115566 A1* | 5/2007 | Miyazawa | G02B 7/02 359/811 |
| 2007/0154198 A1* | 7/2007 | Oh | G02B 7/102 396/85 |
| 2010/0103540 A1* | 4/2010 | An | G02B 7/021 359/819 |
| 2011/0001872 A1* | 1/2011 | Honsho | G02B 7/102 348/362 |
| 2013/0314517 A1* | 11/2013 | Makiyama | A61B 1/045 348/65 |
| 2014/0210976 A1* | 7/2014 | Lin | A61B 1/0011 348/68 |
| 2014/0309495 A1* | 10/2014 | Kirma | G02B 23/243 600/109 |
| 2016/0274350 A1* | 9/2016 | Aizenfeld | G02B 23/2438 |
| 2017/0155808 A1* | 6/2017 | Seger | H04N 5/2257 |
| 2018/0341166 A1* | 11/2018 | Imai | G02B 7/02 |

FOREIGN PATENT DOCUMENTS

| | | | |
|---|---|---|---|
| JP | 5450704 B2 | | 3/2014 |
| JP | 2014230638 A | * | 12/2014 |
| WO | 2015/174406 A1 | | 11/2015 |

\* cited by examiner

IMAGING MODULE, ENDOSCOPE, AND METHOD OF MANUFACTURING IMAGING MODULE

CROSS REFERENCE TO RELATED APPLICATIONS

This application claims priority from Japanese Patent Application No. 2016-52157 filed on Mar. 16, 2016, the contents of which are incorporated herein by reference in their entirety.

BACKGROUND OF THE INVENTION

Field of the Invention

The present invention relate to an imaging module, an endoscope, and a method of manufacturing an imaging module.

Description of the Related Art

An imaging module used in an endoscope or the like is provided with, for example, an image-sensing unit including an image-sensing device and a lens unit (lens) optically connected to the image-sensing device (for example, refer to Japanese Patent No. 5450704, and hereinbelow referred to as Patent Document 1).

In an imaging mechanism disclosed in Patent Document 1, an image-sensing device (particularly, a cover that covers the surface of the image-sensing device) and a lens unit are fixed to each other via an adhesive.

In the imaging mechanism disclosed in Patent Document 1, there is a concern that stability in imaging performance is degraded depending on environmental conditions such as temperature or degree of humidity, and it is desired to increase the stability.

SUMMARY OF THE INVENTION

One aspect of the invention has an object thereof to provide an imaging module, an endoscope, and a method of manufacturing an imaging module, which can stably obtain excellent imaging performance.

An imaging module according to a first aspect of the invention includes: an image-sensing unit that includes an image-sensing device; a lens that has a front end and is optically connected to the image-sensing device; and a frame that is fixed in position with respect to the image-sensing device and includes a lens barrel having an insertion space, into which the front end is to be inserted in at least an optical axis direction. In a state where movement of the lens in a direction intersecting with the optical axis direction is limited, the insertion space is capable of receiving the lens in the direction such that the lens approaches the image-sensing device. The lens is fixed to the lens barrel at a position at which the lens is optically connected to the image-sensing device.

In the imaging module according to the first aspect of the invention, the frame has: a first end at which an insertion opening is formed, the lens being to be inserted into the insertion opening; and a second end at which a positioning hole is formed, the positioning hole determining the position of the image-sensing device so that a light-receiving face is exposed to the insertion space.

The positioning hole may be capable of limiting movement of the image-sensing device in a direction intersecting with the optical axis direction of the image-sensing device.

In the imaging module according to the first aspect of the invention, the frame may include a movement limiter that limits the image-sensing device fixed in position by the positioning hole from moving into the insertion space.

In the imaging module according to the first aspect of the invention, the lens barrel may have one or more slit-shaped cutouts formed in a direction from the first end to the second end.

In the imaging module according to the first aspect of the invention, the frame may be made of a metal.

An endoscope according to a second aspect of the invention includes the imaging module according to the aforementioned first aspect.

A method of manufacturing an imaging module according to a third aspect of the invention, includes: preparing: an image-sensing unit comprising an image-sensing device; a lens having a front end; and a frame comprising a lens barrel having an insertion space into which the front end is to be inserted in at least an optical axis direction, the insertion space being capable of receiving the lens in a direction such that the lens approaches the image-sensing device in a state where movement of the lens in a direction intersecting with the optical axis direction is limited; positioning the image-sensing device of the image-sensing unit and the frame (first step); and inserting the lens into the insertion space and positioning the lens in the lens barrel at a position at which the lens is optically connected to the image-sensing device (second step).

Effects of the Invention

According to the aspects of the invention, since the imaging module includes the frame that can receive the lens in a state where movement of the lens in the direction intersecting with the optical axis is limited, it is possible to fix the position of the lens with a high level of accuracy at the position at which the lens is optically connected to the image-sensing device.

According to the aspects of the invention, since it is not necessary to provide another member interposed between the front end of the lens and image-sensing device, degradation in imaging performance due to environmental conditions such as temperature or degree of humidity, aged deterioration, or the like is less likely to occur as compared with the structure in which a lens is fixed to an image-sensing device via an adhesive.

As a result, it is possible to stably obtain excellent imaging performance.

DETAILED DESCRIPTION OF THE INVENTION

Hereinafter, an embodiment of the invention will be described with reference to drawings.

Imaging Module According to First Embodiment

Figure 1A:
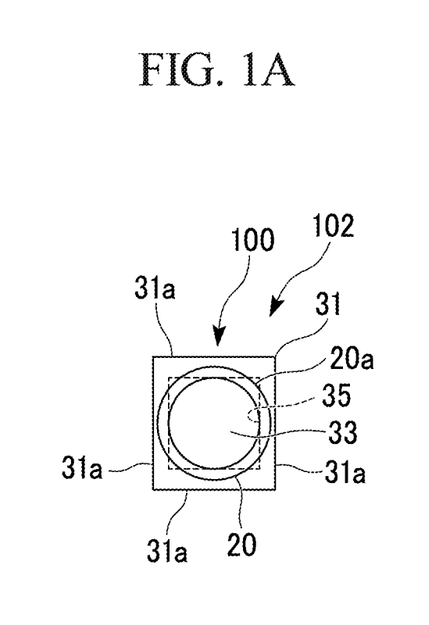
FIG. 1A is a front view showing an imaging module according to the first embodiment.

FIG. 1A is a front view showing an imaging module 100 according to a first embodiment of the invention.

Figure 1B:
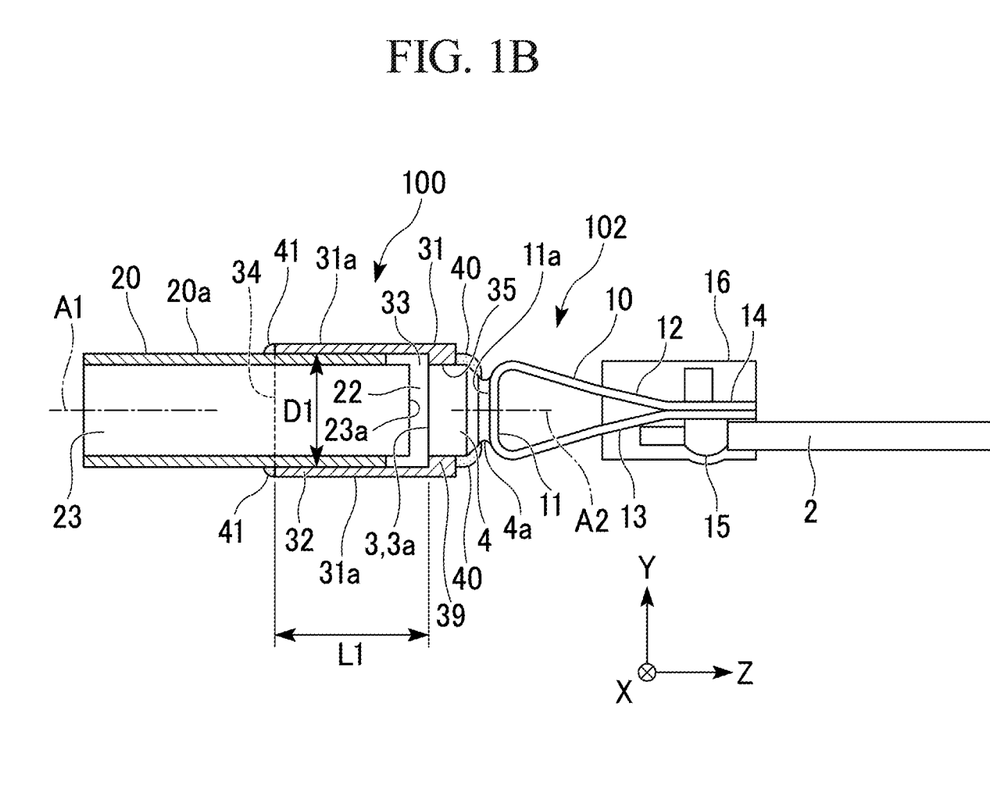
FIG. 1B is a cross-sectional side view showing the imaging module according to the first embodiment.

FIG. 1B is a cross-sectional side view showing the imaging module 100.

Particularly, the position at which an image-sensing device 4 is disposed on a flexible wiring substrate 10 (left side in FIG. 1B) is referred to as a front side, and the opposite side of the front side (right side in FIG. 1B) is referred to as a rear side.

In the following explanation, the XYZ orthogonal coordinate system may be adopted.

The Z-direction is a front-back direction of the imaging module, and the X-direction is a direction orthogonal to the Z-direction and is perpendicular to a paperface in FIG. 1B.

The Y-direction is a direction orthogonal to the X-direction and the Z-direction and is a vertical direction in FIG. 1B.

As shown in FIGS. 1A and 1B, the imaging module 100 includes an image-sensing unit 102, a frame 31, and a lens unit 20 (lens).

The image-sensing unit 102 includes the flexible wiring substrate 10 (wiring part) and the image-sensing device 4 which is mounted on the flexible wiring substrate 10.

The flexible wiring substrate 10 includes: a device-mounted portion 11; and a pair of rear portions 12 and 13 (first rear portion 12 and second the rear portion 13) which are bent at both end portions of the device-mounted portion 11, are directed in the thickness direction of the device-mounted portion, and extend toward the rear side.

Wiring 14 is formed at least on an outer surface of the flexible wiring substrate 10.

As the flexible wiring substrate 10, for example, a flexible wiring substrate having one surface on which wiring is formed can be used.

The front surface (outer surface) of the device-mounted portion 11 is a mount surface 11a on which the image-sensing device 4 is to be mounted.

A conductor 2 is electrically connected via a conductive connector 15 made of solder or the like to the wiring 14 formed on the rear portion 13 of the flexible wiring substrate 10.

The conductor 2 is drawn from, for example, an electrical cable (not shown in the figure).

The back (portion including the conductive connector 15) of the rear portions 12 and 13 of the flexible wiring substrate 10 is covered with an insulating tube 16 having, for example, electrical insulation.

The insulating tube 16 is made of, for example, a resin material such as a silicone resin.

In particular, the flexible wiring substrate 10 is an example of wiring part.

As the image-sensing device 4, for example, CMOS (complementary metal oxide semiconductor) can be preferably used.

The image-sensing device 4 includes an image capturer 3 that is to be optically connected to the lens unit 20.

The image capturer 3 is provided on a front surface of the image-sensing device 4.

The shape of the image-sensing device 4 as seen in the front-back direction is, for example, a rectangular shape (for example, square).

Since the image-sensing device 4 is mounted on the mount surface 11a of the device-mounted portion 11, the image capturer 3 is electrically connected to the wiring 14 of the flexible wiring substrate 10 via an electrical circuit formed in the image-sensing device 4.

The direction of the optical axis A of the image capturer 3 coincides with, for example, the front-back direction.

A light-receiving face 3a of the image capturer 3 is the surface intersecting with the optical axis A1 of the lens unit 20.

The light-receiving face 3a of the image capturer 3 is the surface intersecting with the axis direction of the front end (forward end) of the conductor 2.

The light-receiving face 3a is, for example, a surface along the XY plane.

A bump 4a that is electrically connected to an electrical circuit of the image-sensing device 4 is formed on the back surface of the image-sensing device 4.

The bump 4a is, for example, a solder bump, a stud bump, a plated bump, or the like.

The image-sensing device 4 is electrically connected to the mount surface 11a of the device-mounted portion 11 of the flexible wiring substrate 10 via the bump 4a by use of, for example, a flip-chip method.

The lens unit 20 includes a cylindrical lens barrel 20a; and an object lens 23 that is incorporated into the inside of the lens barrel 20a.

The lens unit 20 is provided in the attitude in which the front end of the lens unit 20 in the direction of the optical axis A1 (the front end 23a of the object lens 23 in the direction of the optical axis A1) is directed to the image-sensing device 4.

The optical axis A1 of the lens unit 20 coincides with the optical axis A2 of the image capturer 3 of the image-sensing device 4.

It is preferable that an outer diameter of the lens unit 20 be smaller than the maximum length of the external shape of the image-sensing device 4 (maximum length of the external shape in the XY plane).

For this reason, since the length of the external shape of the imaging module 100 can be limited, it is possible to reduce the imaging module 100 in size.

Light guided from the front side of the imaging module 100 through the object lens 23 can be imaged by the lens unit 20 on the light-receiving face 3a of the image capturer 3 of the image-sensing device 4.

The lens unit 20 is an example of a lens.

It is preferable that the front end (front end 23a) of the lens unit 20 in the direction of the optical axis A1 be located at the front side of the light-receiving face 3a of the image capturer 3 so as to be separated from the light-receiving face.

A space between the front end 23a and the light-receiving face 3a is an air space 22.

The front end 23a and the light-receiving face 3a are not in contact with each other, and another member is not interposed between the front end 23a and the light-receiving face 3a.

Consequently, a degradation in imaging performance due to environmental conditions such as temperature or degree of humidity, aged deterioration, or the like is less likely to occur as compared with the structure in which a lens unit is fixed to an image-sensing device via an adhesive.

As shown in FIGS. 2A to 2D, the frame 31 includes: a wall end 39 which is formed in a rectangular plate shape; and a lens barrel 32 which extends forward from the peripheral edge portion of the wall end 39.

The wall end 39 is formed at the rear end of the frame 31 (the other end, second end).

Figure 2A:
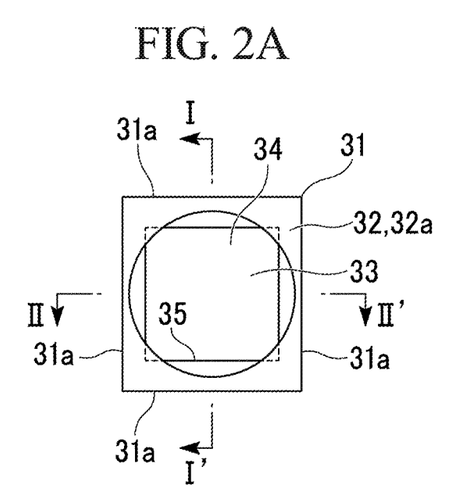
FIG. 2A is a view showing a frame of the imaging module according to the first embodiment and is a front view showing a frame.

The lens barrel 32 has an external appearance that is formed in a square tubular shape having four planar outer surfaces 31a.

An opening of the front end of the lens barrel 32 (one end, first end) is referred to as an insertion opening 34.

An internal space of the lens barrel 32 is an insertion space 33 into which the lens unit 20 is to be inserted.

The insertion space 33 is formed in, for example, a cylindrical shape having the central axis extending in the front-back direction, and the cross-sectional shape of the insertion space is circular in shape.

As shown in FIG. 1B, it is preferable that an internal diameter (length of the internal shape) of the insertion space 33 be substantially the same as the outer diameter (the length of the external shape) of the lens unit 20 or slightly larger than the outer diameter of the lens unit 20.

Because of this, since the inner surface of the insertion space 33 comes into contact with or comes close to the outer surface of the lens unit 20, it is possible to limit movement of the lens unit 20 in the direction intersecting with the direction of the optical axis A1.

Consequently, the position of the lens unit 20 in the XY plane does not vary.

Particularly, the direction intersecting with the direction of the optical axis A1 is, for example, a direction orthogonal to the direction of the optical axis A1 such as X-direction or Y-direction.

Since the insertion space 33 can limit movement of the lens unit 20 in the direction intersecting with the direction of the optical axis A1, it is possible to limit the lens unit 20 from tilting.

Accordingly, the direction of the optical axis A1 of the lens unit 20 does not vary.

The insertion space 33 is configured to receive the lens unit 20 in a state where the lens unit 20 can be movable in the direction such that it comes close to or approaches the image-sensing device 4 and can accommodate the portion including the front end (front end 23a) at least in the direction of the optical axis A1 of the lens unit 20.

Figure 2B:
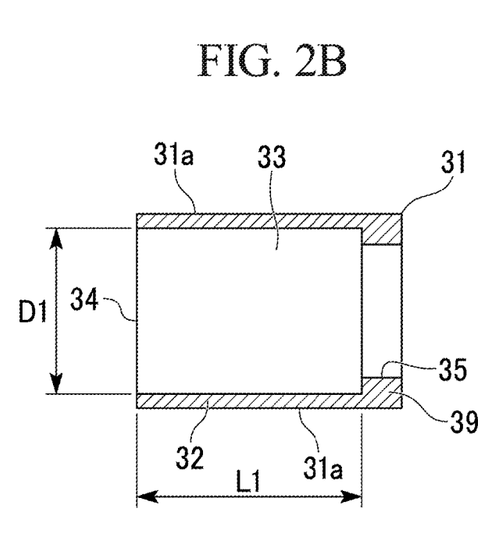
FIG. 2B is a view showing the frame of the imaging module according to the first embodiment and is a cross-sectional view taken along the line I-I' shown in FIG. 2A.

The length L1 of the lens barrel 32 in the front-back direction can be determined to be, for example, 1.5 times or more of the internal diameter D1 of the lens barrel 32.

Consequently, since the insertion length of the lens unit 20 can be sufficiently ensured, it is possible to prevent the lens unit 20 from tilting.

The length L1 can be determined to be, for example, three times or less of the internal diameter D1.

It is preferable that the length L1 be determined so that part of the lens unit 20 protrudes forward from the lens barrel 32.

The protruding length of the lens unit 20 from the lens barrel 32 can be determined to be, for example, one-third or more of the overall length of the lens unit 20.

In the case where part of the lens unit 20 protrudes from the lens barrel 32, since it is possible to hold the lens unit 20 by this protruding portion, operation of adjusting the position of the lens unit 20 in the front-back direction becomes easy.

The lens unit 20 that is inserted into the insertion space 33 is fixed to the lens barrel 32 at the position at which the lens unit is optically connected to the image-sensing device 4.

The lens unit 20 can be fixed to the lens barrel 32 by use of, for example, an adhesive 41 (described below) or the like.

The center position of the image-sensing area of the light-receiving face 3a of the image-sensing device 4 may be displaced from the center of the front surface (surface including the light-receiving face 3a) of the image-sensing device 4 (decentering position).

Particularly, in the case where the size of the image-sensing device 4 is small, in many cases in designing an image-sensing device, it is necessary to displace the center position of the image-sensing area from the center of the image-sensing device 4.

In this case, the position at which the insertion space 33 is to be formed in the XY plane can be the decentering position which corresponds to the position of the image-sensing area of the image-sensing device 4.

That is, even in cases where the image-sensing device 4 is decentered in the imaging module 100, it is possible to optically connect the lens unit 20 to the image-sensing device 4 with a high degree of accuracy by designing the lens barrel 32 of the frame 31 so as to correspond to the decentering position thereof.

In the case where the outer diameter of the lens unit 20 is smaller than the length of the external shape of the image-sensing device 4, the influence of the displacement due to decentering (for example, displacement in an optical axis position) on imaging performance is likely to be larger as compared with the case where the outer diameter of the lens unit 20 is larger.

In contrast, since the frame 31 is used in the imaging module 100, the aforementioned displacement does not occur, and even in cases where an outer diameter of the lens unit 20 is small, it is possible to optically connect the lens unit 20 and the image-sensing device 4 with a high degree of accuracy.

Figure 2C:
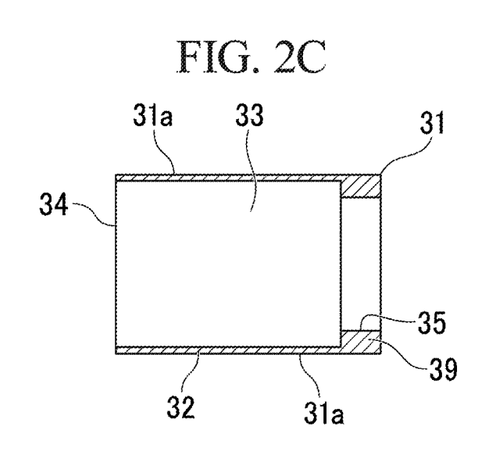
FIG. 2C is a view showing the frame of the imaging module according to the first embodiment and is a cross-sectional view taken along the line II-II' shown in FIG. 2A.
Figure 2D:
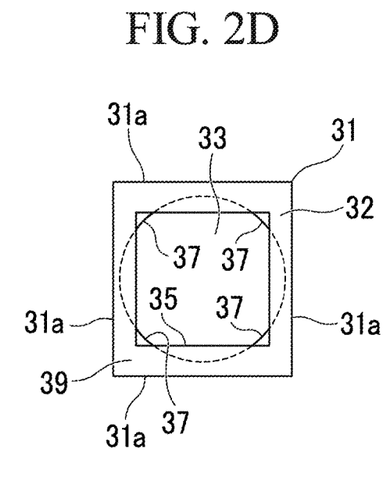
FIG. 2D is a view showing the frame of the imaging module according to the first embodiment and is a rear view showing the frame.

As shown in FIGS. 2B to 2D, a positioning hole 35 into which the image-sensing device 4 is to be inserted is formed on the wall end 39.

The positioning hole 35 is formed so as to be able to limit the image-sensing device 4 from moving in a direction intersecting with the front-back direction (i.e., a direction intersecting with the optical axis A2 of the image-sensing device 4).

It is preferable that the inner surface of the positioning hole 35 come into contact with or come close to the side surface of the image-sensing device 4 at least two points different from each other.

Consequently, it is possible to limit movement of the image-sensing device 4 in a plurality of different directions which are directions intersecting with the front-back direction.

For example, the positioning hole 35 is formed in a rectangular shape (for example, square shape) as seen from rear (refer to FIG. 2D).

As long as the side surface of the image-sensing device 4 comes into contact with or comes close to the inner surfaces corresponding to the adjacent two sides of the four sides of the positioning hole 35, it is possible to limit the image-sensing device 4 from moving in a plurality of different directions.

It is preferable that the length of the internal shape (for example, the length of one side of the rectangular shape) of the positioning hole 35 be substantially the same as the length of the external shape of the image-sensing device 4 (for example, the length of one side of the rectangular shape) or slightly larger than the length of the external shape of the image-sensing device 4.

As a result, since the side surface of the image-sensing device 4 comes into contact with or comes close to the inner surfaces corresponding to the four sides of the positioning hole 35, movement of the image-sensing device 4 in the direction intersecting with the front-back direction (for example, a direction along the XY plane) is limited.

Consequently, the position of the image-sensing device 4 in the XY plane does not vary.

As shown in FIG. 1B, the positioning hole 35 penetrates through the wall end 39, and the light-receiving face 3a of the image-sensing device 4 that is inserted into the positioning hole 35 can be disposed at the position at which the light-receiving face 3a is exposed to the insertion space 33.

The positioning hole 35 is formed so that the optical axis A2 of the image-sensing device 4 coincides with the optical axis A1 of the lens unit 20 provided in the insertion space 33.

As shown in FIG. 2D, the length of the diagonal line of the positioning hole 35 formed in a rectangular shape is longer than the length of the internal shape (internal diameter) of the insertion space 33.

Therefore, a stepped portion due to a difference in length of the internal shape between the positioning hole 35 and the insertion space 33 is formed at the portion of the positioning hole 35 which includes four corners, and the back surface of the stepped portion is a movement limiter 37 that limits the image-sensing device 4 inserted into the positioning hole 35 from moving into the insertion space 33.

The movement limiter 37 is a contact face parallel to, for example, the XY plane.

Since the movement limiter 37 is formed at each of the four corners of the positioning hole 35, the image-sensing device 4 comes into contact with the movement limiter 37 at the four corner portions, and the movement limiter 37 is fixed in position with a high degree of accuracy.

It is preferable that the frame 31 be made of a metal such as stainless steel or an aluminum alloy.

In the case where the frame 31 made of a metal, since a degree of rigidity and a surface hardness of the frame 31 can be higher, it is possible to improve accuracy of positioning of the lens unit 20 with respect to the image-sensing device 4.

Figure 3:
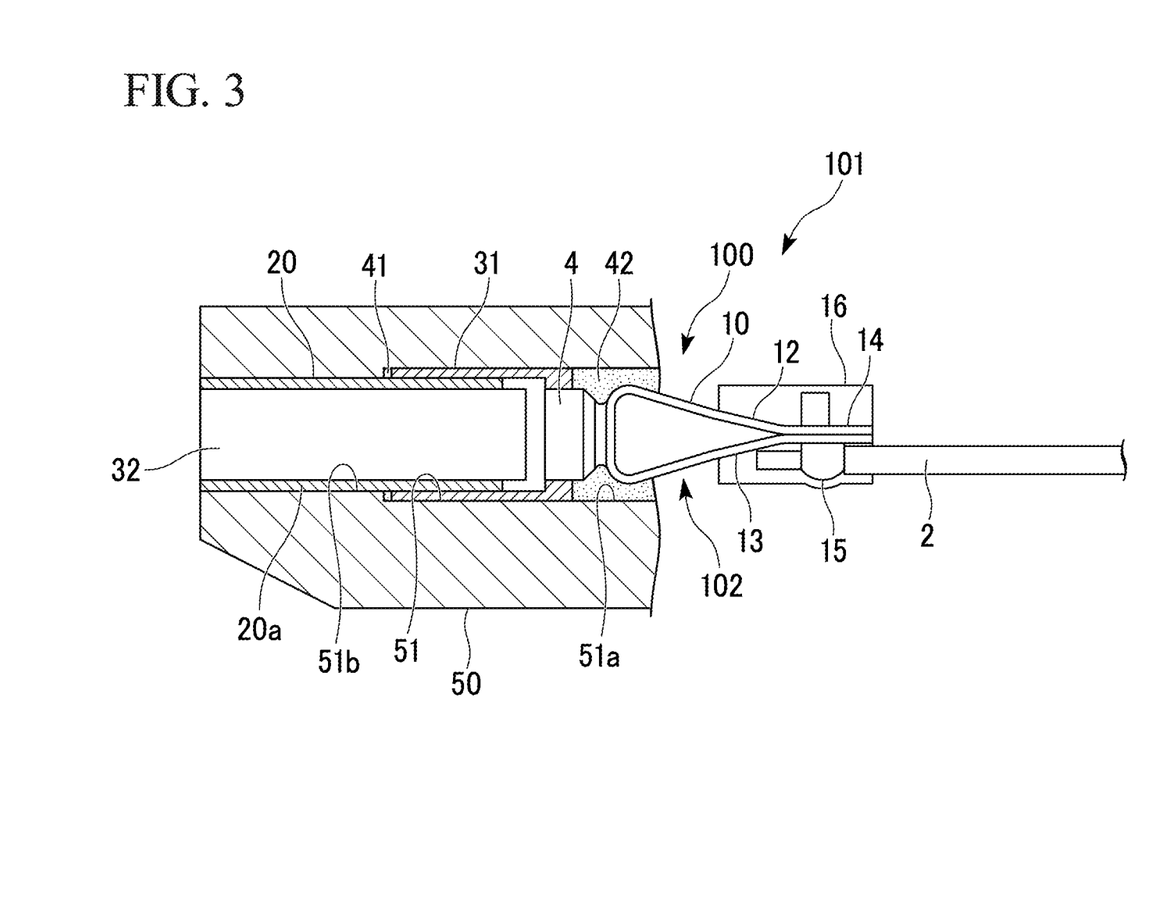
FIG. 3 is a cross-sectional view showing a front-end structure of an endoscope using the imaging module according to the first embodiment.

It is possible to dispose the lens unit 20 and the image-sensing device 4 at a desired position of a housing 50 by designing the frame 31 so as to comply with an attachment hole 51 of the housing 50 (refer to FIG. 3).

(Endoscope)

FIG. 3 is a cross-sectional view showing a front-end structure of an endoscope 101 using the imaging module 100.

The endoscope 101 has a front-end structure including the housing 50 and the imaging module 100 provided inside the attachment hole 51 of the housing 50.

The attachment hole 51 includes: the frame 31; a first insertion portion 51a through which the image-sensing device 4 or the like is inserted; and a second insertion portion 51b through which part of the lens unit 20 is inserted.

The length of the internal shape of the first insertion portion 51a is substantially the same as the length of the external shape of the frame 31 or is slightly larger than the length of the external shape of the frame 31.

The length of the internal shape (internal diameter) of the second insertion portion 51b is substantially the same as the length of the external shape (outer diameter) of the lens unit 20 or is larger than the length of the external shape of the lens unit 20.

The first insertion portion 51a may be filled with an adhesive 42.

The inner surface of the second insertion portion 51b can be adhesively-fixed to the outer surface of the lens unit 20 by an adhesive (not shown in the figure).

As long as the accuracy of the length of the external shape of the frame 31 is sufficiently higher than that of the length of the internal shape of the first insertion portion 51a, even where the accuracy of the lengths of other elements constituting the imaging module 100 is low, it is possible to accurately fix the position of the imaging module 100 with respect to the housing 50.

For example, a high degree of accuracy is not required for the length of the second insertion portion 51b, and even where a space is provided between the inner surface of the second insertion portion 51b and the outer surface of the lens unit 20, no problems occur.

Since a high machining accuracy is not required for the portions other than the frame 31 and the portion (first insertion portion 51a) of the housing 50 which corresponds to the frame 31, the manufacture of the imaging module 100 and the housing 50 becomes easy, and it is possible to improve the manufacturing yield thereof.

Since the imaging module 100 uses the frame 31, it is possible to design the frame 31 in accordance with the position or the like of the lens unit 20 which is required to correspond to the product specification of the endoscope 101.

For example, by designing the shape or the like of the frame 31 in accordance with the housing 50, it is possible to dispose the lens unit 20 at a desired position.

Additionally, in the case where another functional part is built in the housing 50 near the imaging module 100, by use of a frame 31 having the shape that can avoid the functional part, it is possible to dispose the lens unit 20 at a desired position.

As stated above, in the imaging module 100, since it is possible to form the frame 31 in shape corresponding to the housing 50, it is possible to accurately dispose the lens unit 20 or the like at a required position.

(Method of Manufacturing Imaging Module)

Next, a method of manufacturing the imaging module 100 and a method of manufacturing the endoscope 101 will be described with reference to FIGS. 4A to 6B.

(First Step)

Figure 4A:
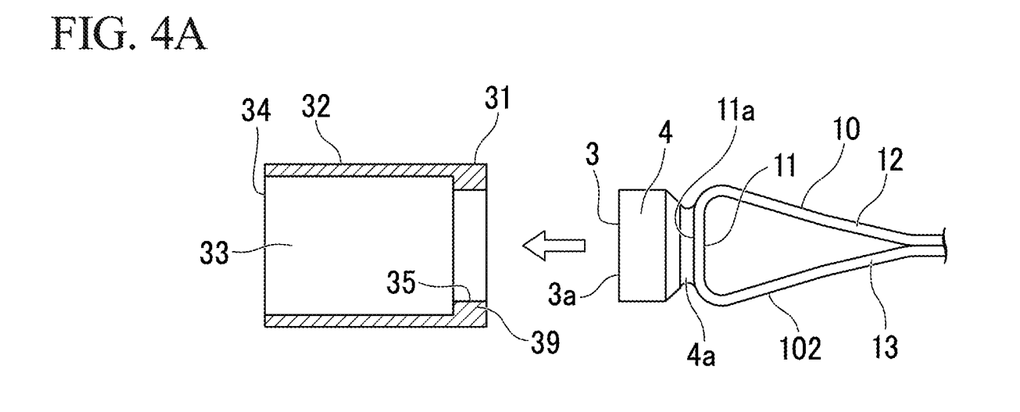
FIG. 4A is an explanatory view showing a method of manufacturing the imaging module according to the first embodiment.
Figure 4B:
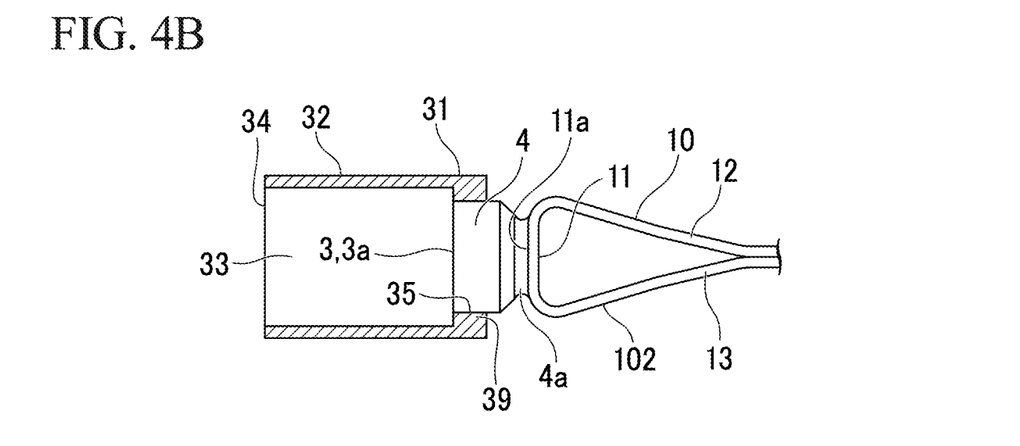
FIG. 4B is an explanatory view showing the method of manufacturing the imaging module according to the first embodiment.

As shown in FIGS. 4A and 4B, the image-sensing device 4 of the image-sensing unit 102 is inserted into the positioning hole 35 of the frame 31 from the back.

The image-sensing device 4 moves forward until coming into contact with the movement limiter 37 (refer to FIG. 2D).

Movement of the image-sensing device 4 in the direction intersecting with the front-back direction (for example, in a direction perpendicular to the paperface and a vertical direction shown in FIGS. 4A and 4B) is limited by the positioning hole 35, and forward movement of the image-sensing device 4 is limited by the movement limiter 37.

Consequently, the image-sensing device 4 is fixed in position so that the light-receiving face 3a is exposed to the insertion space 33.

Figure 4C:
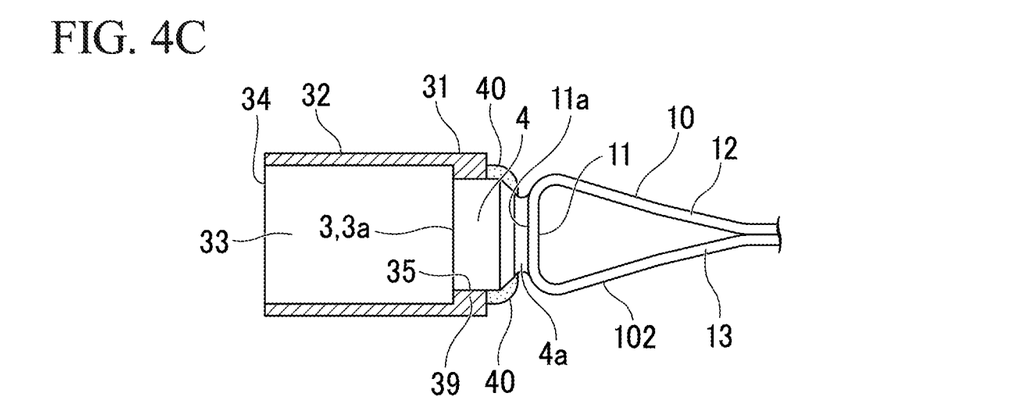
FIG. 4C is an explanatory view showing the method of manufacturing the imaging module according to the first embodiment.

Next, as shown in FIG. 4C, an adhesive 40 is applied over the region which is from part of the external surface of the wall end 39 including the peripheral edge portion of the positioning hole 35 to part of the external surface of the image-sensing device 4.

Part of the adhesive 40 may enter a gap between the external surface of the image-sensing device 4 and the inner surface of the positioning hole 35.

By curing the adhesive 40, the image-sensing device 4 is fixed to the frame 31.

Since the adhesive 40 is applied onto the wall end 39 and the external surface of the image-sensing device 4, the adhesive is less likely to reach the front surface of the image-sensing device 4.

Accordingly, the adhesive 40 does not adversely affect optical connection between the lens unit 20 and the image-sensing device 4.

(Second Step)

Figure 5A:
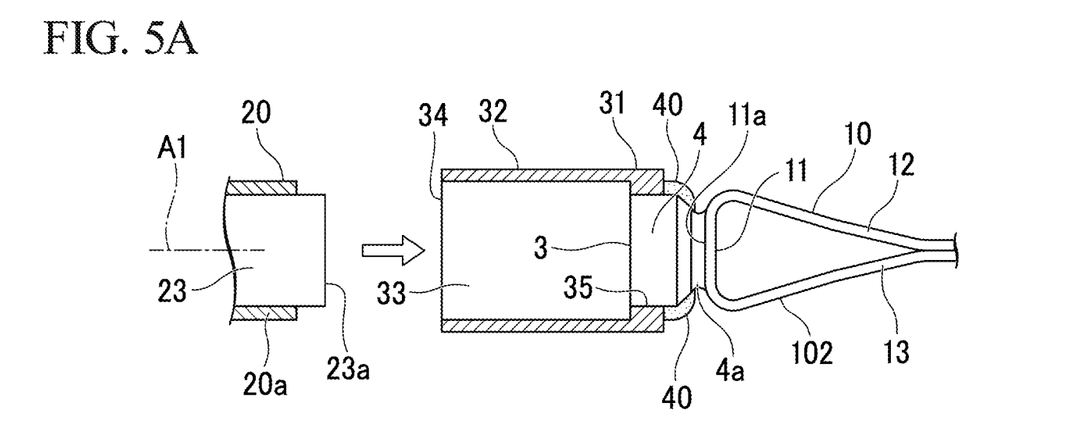
FIG. 5A is an explanatory view showing the method of manufacturing the imaging module according to the first embodiment.
Figure 5B:
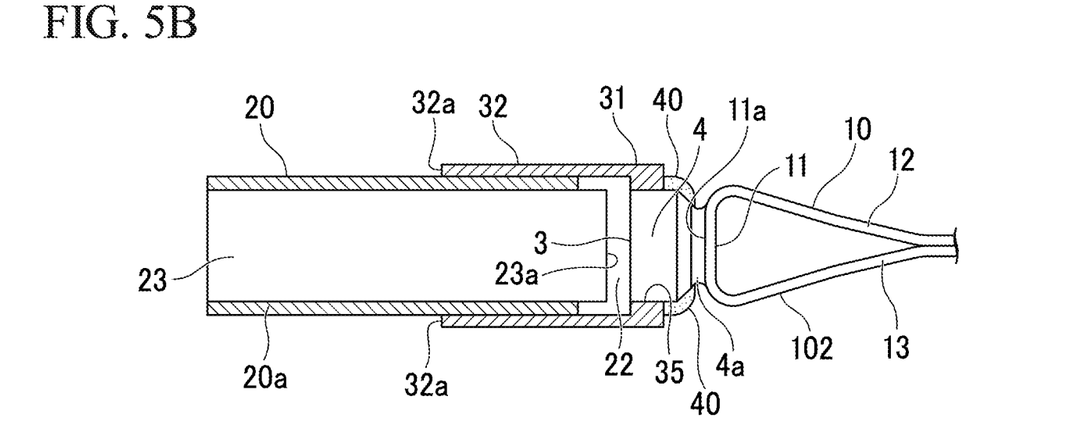
FIG. 5B is an explanatory view showing the method of manufacturing the imaging module according to the first embodiment.

Subsequently, as shown in FIGS. 5A and 5B, the lens unit 20 passes through the insertion opening 34, is inserted into the insertion space 33 from the front end 23a in the direction of the optical axis A1, and moves rearward.

In this situation, the lens unit 20 is inserted into the insertion space 33 while the movement of the lens unit 20 in the direction intersecting with the direction of the optical axis A1 (for example, in a direction perpendicular to the paperface and a vertical direction shown in FIGS. 5A and 5B) is being limited.

In a state where the lens unit 20 is inserted into the insertion space 33, the optical axis A1 of the lens unit 20 coincides with the optical axis A2 of the image capturer 3 of the image-sensing device 4.

As shown in FIG. 5B, the lens unit 20 is fixed in position to the lens barrel 32 at the position at which the lens unit is optically connected to the image-sensing device 4.

It is preferable that the front end 23a of the lens unit 20 be located separately from the light-receiving face 3a of the image capturer 3.

The position of the lens unit 20 in the front-back direction can be determined in accordance with the resolution capability of the image obtained by the image-sensing device 4.

For example, it is possible to dispose the lens unit 20 at the position at which the resolution capability of the image obtained by the image-sensing device 4 is substantially coincident with the preliminarily-obtained result by simulation.

Figure 5C:
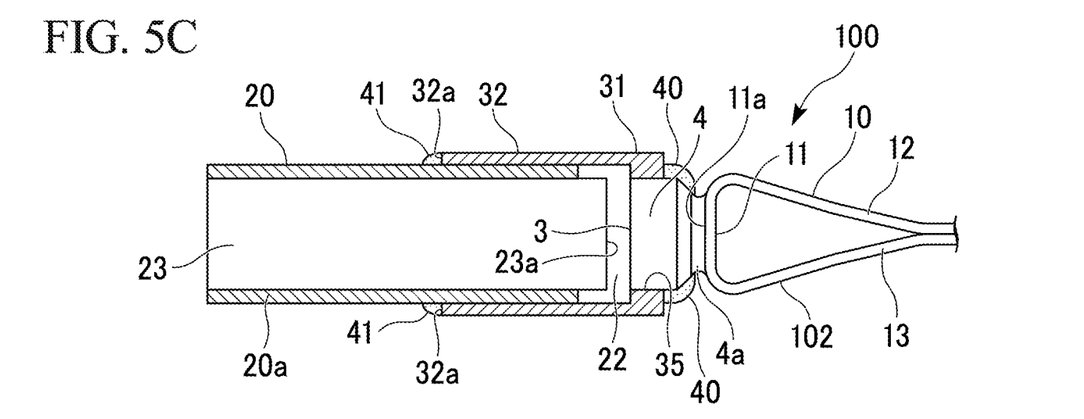
FIG. 5C is an explanatory view showing the method of manufacturing the imaging module according to the first embodiment.

Next, as shown in FIG. 5C, the adhesive 41 is applied over the region which is from the front-end portion 32a of the lens barrel 32 of the frame 31 to part of the outer surface of the lens unit 20.

By curing the adhesive 40, the lens unit 20 is fixed to the frame 31.

Accordingly, the image-sensing unit 102 shown in FIGS. 1A and 1B is obtained.

(Third Step)

Figure 6A:
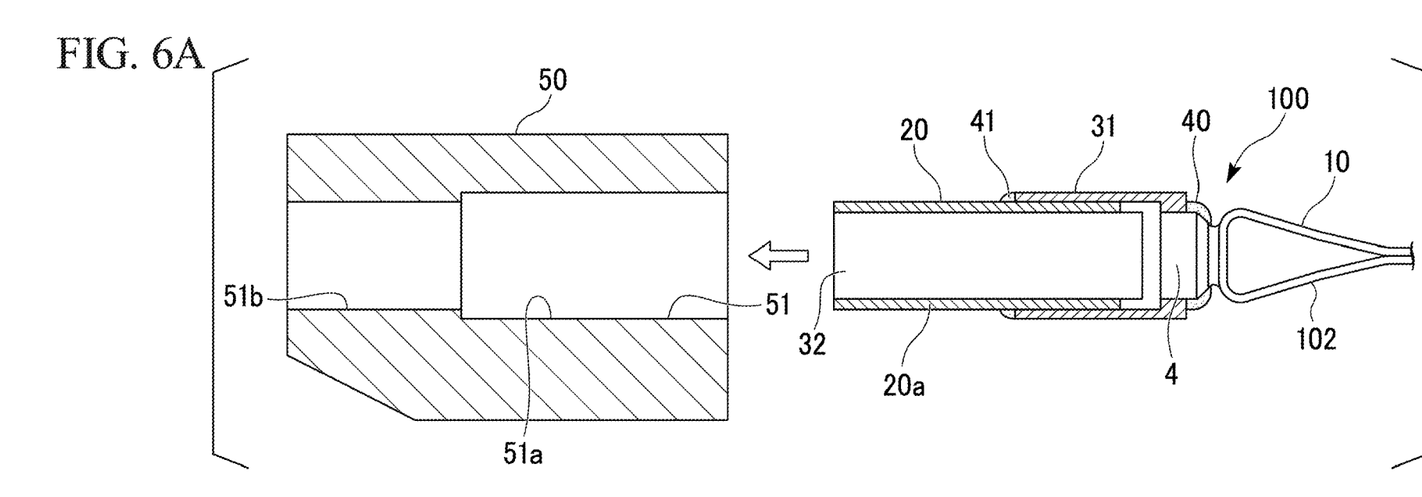
FIG. 6A is an explanatory view showing the method of manufacturing the imaging module according to the first embodiment.
Figure 6B:
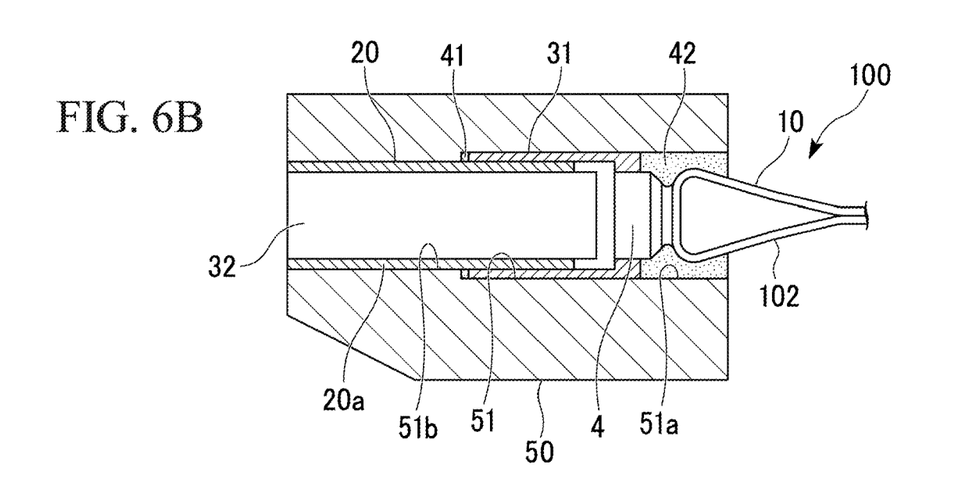
FIG. 6B is an explanatory view showing the method of manufacturing the imaging module according to the first embodiment.

Subsequently, as shown in FIG. 6A, the image-sensing unit 102 is inserted from the rear side into the attachment hole 51 formed on the housing 50.

The frame 31, the image-sensing device 4, and the like are disposed inside the first insertion portion 51a, and part of the lens unit 20 is disposed inside the second insertion portion 51b.

The first insertion portion 51a can be filled with the adhesive 42.

The outer surface of the lens unit 20 can be adhesively-fixed to the inner surface of the second insertion portion 51b by an adhesive (not shown in the figure).

As a result, the endoscope 101 shown in FIG. 3 is obtained.

Accordingly, since the imaging module 100 includes the frame 31 that can receive the lens unit 20 in a state where the movement of the lens unit 20 in the direction intersecting with the optical axis A1 is limited, it is possible to fix the position of the lens unit 20 with a high level of accuracy at the position at which the lens unit 20 is optically connected to the image-sensing device 4.

In the imaging module 100, since it is not necessary to provide another member interposed between the front end 23a of the lens unit 20 and the image-sensing device 4, degradation in imaging performance due to environmental conditions such as temperature or degree of humidity, aged deterioration, or the like is less likely to occur as compared with the structure in which a front end of a lens unit is fixed to an image-sensing device.

Consequently, in the imaging module 100, it is possible to stably obtain excellent imaging performance.

In the imaging module 100, since the positioning hole 35 that determines the position of the image-sensing device 4 is formed on the wall end 39 of the frame 31 so that the light-receiving face 3a is exposed to the insertion space 33, it is possible to fix the position of the image-sensing device 4 with respect to the lens unit 20 with a high degree of accuracy.

Since the movement limiter 37 that limits movement of the image-sensing device 4 is formed on the frame 31, it is possible to fix the position of the image-sensing device 4 with respect to the lens unit 20 with a high degree of accuracy.

Since the image-sensing device 4 is only inserted into the positioning hole 35, it is easy to dispose the image-sensing device 4 at the position that is to be in contact with the movement limiter 37.

Accordingly, it is possible to determine the position of the image-sensing unit 102 with a high degree of accuracy in the front-back direction.

Since the aforementioned method of manufacturing the imaging module 100 includes: the first step of positioning the image-sensing device 4 and the frame 31; and the second step of positioning the lens unit 20 and the frame 31, it is possible to fix the position of the image-sensing device 4 with respect to the lens unit 20 with a high degree of accuracy.

Since it is possible to assemble the imaging module 100 before being incorporated into the housing 50, it is possible to adjust the position of the imaging module 100 in the housing 50 by adjusting the insertion depth thereof with respect to the attachment hole 51.

Consequently, in the case where, for example, there is a design limitation such that protrusion of the lens unit 20 from the housing 50 is not allowed in the endoscope 101, even where the sizes of a component slightly vary, it is possible to easily avoid an occurrence of a defect product having the lens unit 20 protruding from the housing 50, by adjusting the position of the imaging module 100 in the housing 50.

Therefore, it is possible to improve the manufacturing yield thereof.

Imaging Module According to Second Embodiment

Figure 7A:
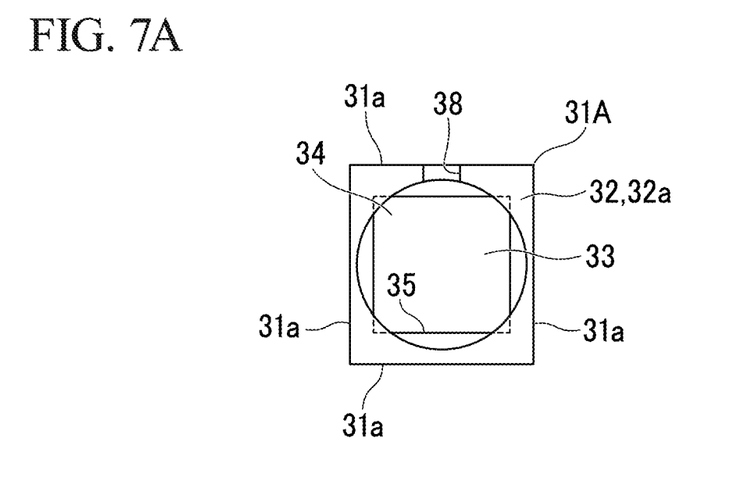
FIG. 7A is a front view showing an imaging module according to a second embodiment and is a view showing a state where a lens unit is removed from the imaging module.

FIG. 7A is a front view showing an imaging module 100A according to a second embodiment of the invention.

The imaging module 100A is in a state where the lens unit 20 is removed therefrom.

Figure 7B:
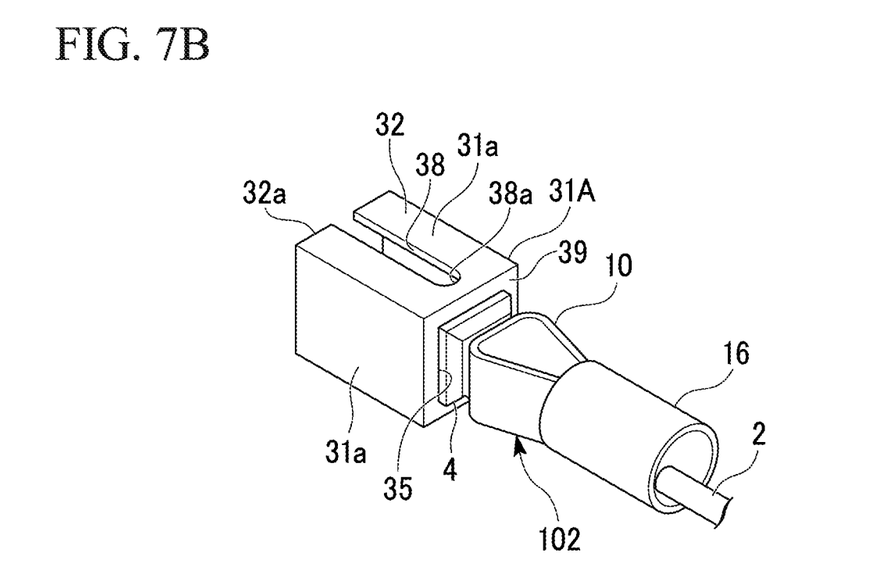
FIG. 7B is a perspective view showing the imaging module according to the second embodiment and is a view showing a state where the lens unit is removed from the imaging module.

FIG. 7B is a perspective view showing the imaging module 100A in a state where the lens unit 20 is removed therefrom.

Figure 8:
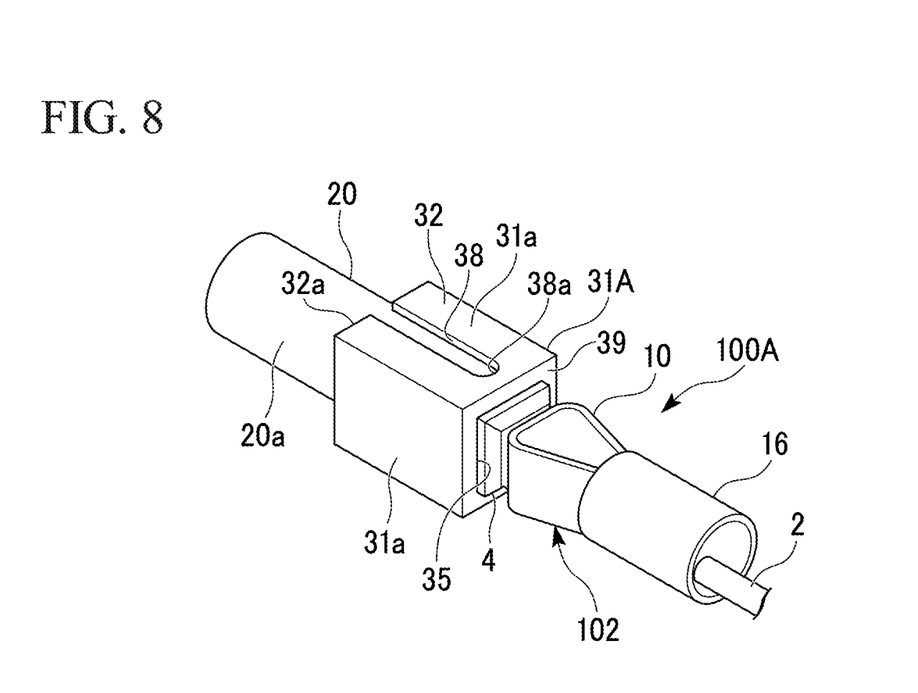
FIG. 8 is a perspective view showing the imaging module according to the second embodiment and is a view showing a state where the lens unit is inserted into a frame.

FIG. 8 is a perspective view showing the imaging module 100A in a state where the lens unit 20 is inserted into a frame 31A.

As shown in FIGS. 7A, 7B, and 8, the imaging module 100A is different from the imaging module 100 shown in FIGS. 1A, 1B, and the like in that the frame 31A having a slit-shaped cutout 38 is used.

The cutout 38 is formed to be directed rearward from the front-end portion 32a in front-back direction.

The cutout 38 may be formed in a shape having, for example, a fixed width.

For example, the cutout 38 is formed on one of four external surfaces 31a of the lens barrel 32 and at the position corresponding to the center in the width direction thereof (in the horizontal direction shown in FIG. 7A).

In other cases, as shown in FIG. 7A, the cutout 38 may be formed at one portion of the lens barrel 32 and may be formed at a plurality of portions of the lens barrel 32.

For example, in FIG. 7A, a second cutout having the same shape as that of the cutout 38 may be provided at the position opposite to the cutout 38 with the insertion space 33 interposed therebetween.

The number of cutouts may be optionally selected such as two or more.

The position of the end 38a (rear end) of the cutout 38 (position in the front-back direction) is determined so that external light does not enter the inside of the frame 31 through the cutout 38.

As shown in FIG. 8, since the cutout 38 is blocked by the outer surface of the lens unit 20 in the imaging module 100A, external light does not enter the inside of the frame 31.

Therefore, it does not adversely affect an image to be obtained by the image-sensing device 4.

In the imaging module 100A, since the frame 31A has the cutout 38, the portion having the front-end portion 32a of the lens barrel 32 is slightly and elastically deformable in a direction in which the width of the cutout 38 increases or decreases.

Therefore, by appropriately determining the internal diameter of the insertion space 33, it is possible to provide a function of holding the lens unit 20 due to an elastic force to the lens barrel 32.

According to this configuration, since it is possible to temporarily fix the position of the lens unit 20 by an elastic force of the lens barrel 32, it is possible to easily adjust the position of the lens unit 20 in the front-back direction.

Since the frame 31A has the cutout 38, when the lens unit 20 is inserted into the insertion space 33, it is possible to remove air inside the insertion space 33 through the cutout 38 to the outside from the insertion space.

For this reason, it is possible to avoid the lens unit 20 from being difficult to be inserted into the insertion space 33 due to an increase in pressure inside the insertion space 33.

Next, a frame 61 which is a modified example of the frame 31 will be described with reference to FIGS. 9A to 9D.

As shown in FIGS. 9A to 9D, the frame 61 is configured so that, the external surface 61a that is one of four external surfaces of the lens barrel 32 is formed in a curved protrusion shape in cross section (arc shape) in accordance with a design limitation of a housing (not shown in the figure).

Figure 9A:
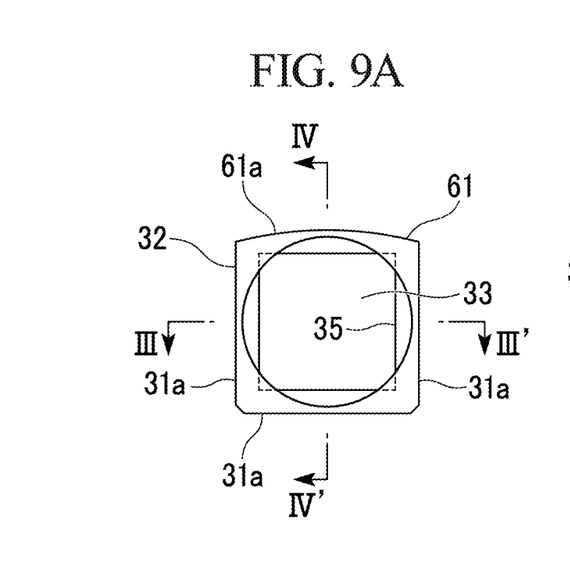
FIG. 9A is a view showing a modified example according to a frame and is a front view showing the frame.
Figure 9B:
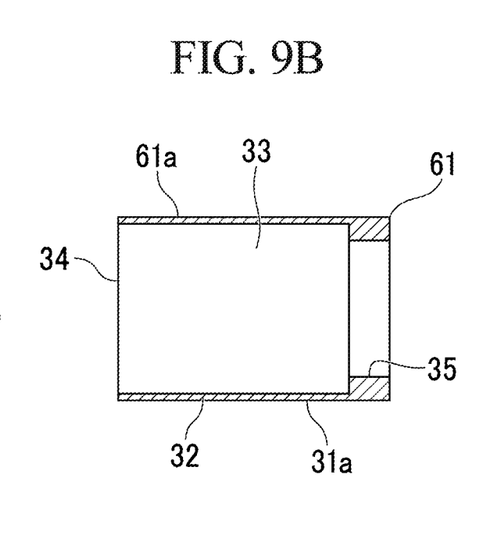
FIG. 9B is a view showing a modified example according to a frame and is a cross-sectional view III-III' shown in FIG. 9A.
Figure 9C:
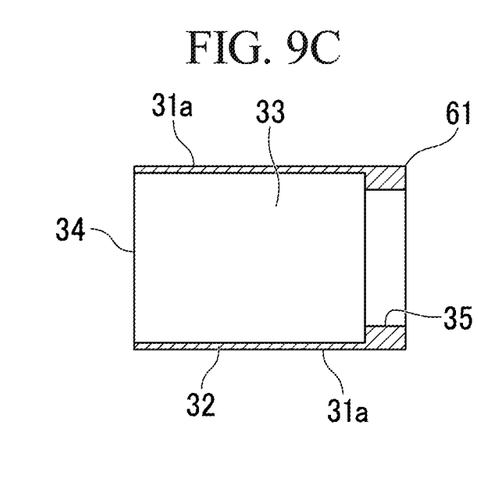
FIG. 9C is a view showing a modified example according to a frame and is a cross-sectional view IV-IV' shown in FIG. 9A.
Figure 9D:
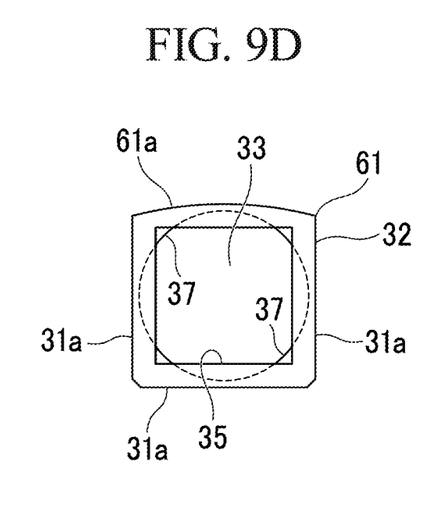
FIG. 9D is a view showing a modified example according to a frame and is a rear view showing the frame.

For example, in the case where an attachment hole (not shown in the figure) is formed on a housing and has an inner surface formed in a curved recessed shape, it is possible to incorporate the frame 61 into the inner surface so as to match the external surface 61a to the inner surface.

Accordingly, the imaging module 100A is prevented from being incorrectly positioned in a direction around light axis, and it is possible to incorporate the imaging module 100A into the housing 50 at a right position.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

For example, the lens barrel 32 of the frame 31 may have a length such that it is possible to accommodate the entire lens unit 20 therein.

In the above-mentioned method of manufacturing the imaging module 100, the second step of fixing the positions of the frame 31 and the lens unit 20 is carried out after the first step of fixing the positions of the image-sensing device 4 and the frame 31; however, the order of carrying out the first step and the second step is not particularly limited.

For example, the first step may be carried out after the second step, or the first step and the second step may be simultaneously carried out.

What is claimed is:

1. An imaging module comprising:
   an image-sensing-device mounted substrate that comprises a wiring substrate and an image-sensing device mounted on the wiring substrate;
   a lens that has a front end and is optically connected to the image-sensing device; and
   a frame that is fixed in position with respect to the image-sensing device and comprises a lens barrel having an insertion space into which the front end is to be inserted in at least an optical axis direction, the frame having a positioning hole determining a position of the image-sensing device, wherein
   in a state where movement of the lens in a direction intersecting with the optical axis direction is limited, the insertion space is capable of receiving the lens in a direction such that the lens approaches the image-sensing device,
   the lens is fixed to the lens barrel at a position at which the lens is optically connected to the image-sensing device,
   the positioning hole has a movement limiter that is formed in the positioning hole, and is a contact face parallel to the direction intersecting with the optical axis direction, the positioning hole has an inner surface that comes into contact with or comes close to a side surface of the image-sensing device,
   the movement limiter limits the image-sensing device from moving into the insertion space by coming into contact with or coming close to a light-receiving face of the image-sensing device,
   as viewed from the optical axis direction, in an area where the movement limiter is formed in radial direction that revolves around the optical axis direction, a first distance between a furthest point on the inner surface of the positioning hole and a center of the positioning hole is longer than a second distance between an inner surface of the lens barrel and a center of the lens barrel, and
   as viewed from the optical axis direction, a third distance between a closest point on the inner surface of the positioning hole and the center of the positioning hole is smaller than the second distance.

2. The imaging module according to claim 1, wherein the frame has:
   a first end at which an insertion opening is formed, the lens being to be inserted into the insertion opening; and
   a second end at which the positioning hole is formed, wherein
   the positioning hole determines the position of the image-sensing device so that the light-receiving face is exposed to the insertion space, and
   the positioning hole is capable of limiting movement of the image-sensing device in a direction intersecting with the optical axis direction of the image-sensing device.

3. The imaging module according to claim 2, wherein the lens barrel has one or more slit-shaped cutouts formed in a direction from the first end to the second end.

4. The imaging module according to claim 1, wherein the frame is made of a metal.

5. An endoscope comprising the imaging module according to claim 1.

6. A method of manufacturing an imaging module, comprising:
   preparing: an image-sensing-device mounted substrate comprising a wiring substrate and an image-sensing device mounted on the wiring substrate; a lens having a front end; and a frame comprising a lens barrel having an insertion space into which the front end is to be inserted in at least an optical axis direction, the insertion space being capable of receiving the lens in a direction such that the lens approaches the image-sensing device in a state where movement of the lens in a direction intersecting with the optical axis direction is limited wherein the frame has a positioning hole determining a position of the image-sensing device and the positioning hole has an inner surface;
   adjusting the position of the image-sensing device of the image-sensing-device mounted substrate in the positioning hole of the frame in the direction intersecting with the optical axis direction by causing the inner surface of the positioning hole to come into contact with or come close to a side surface of the image-sensing device;
   limiting the image-sensing device from moving into the insertion space by a movement limiter which is formed in the positioning hole, and which has a contact face parallel to the direction intersecting with the optical axis direction, wherein the movement limiter comes into contact with or comes close to a light-receiving face of the image-sensing device,
   inserting the lens into the insertion space and positioning the lens in the lens barrel at a position at which the lens is optically connected to the image-sensing device, wherein
   as viewed from the optical axis direction, in an area where the movement limiter is formed in radial direction that revolves around the optical axis direction, a first distance between a furthest point on the inner surface of the positioning hole and a center of the positioning hole is longer than a second distance between an inner surface of the lens barrel and a center of the lens barrel, and
   as viewed from the optical axis direction, a third distance between a closest point on the inner surface of the positioning hole and the center of the positioning hole is smaller than the second distance.

* * * * *